United States Patent
Foster

(10) Patent No.: US 6,521,647 B2
(45) Date of Patent: Feb. 18, 2003

(54) TREATMENT OF RENAL DISORDERS

(75) Inventor: Adrian Paul Foster, Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/818,403

(22) Filed: Mar. 27, 2001

(65) Prior Publication Data

US 2001/0036954 A1 Nov. 1, 2001

Related U.S. Application Data

(60) Provisional application No. 60/198,415, filed on Apr. 19, 2000.

(30) Foreign Application Priority Data

Apr. 4, 2000 (GB) .............................................. 0008332

(51) Int. Cl.$^7$ .............................................. A61K 31/44
(52) U.S. Cl. ...................................................... 514/356
(58) Field of Search ......................................... 514/356

(56) References Cited

U.S. PATENT DOCUMENTS

| | | | | |
|---|---|---|---|---|
| 4,879,303 A | * | 11/1989 | Davison et al. .............. | 514/356 |
| 5,270,323 A | * | 12/1993 | Milne, Jr. et al. ........... | 514/309 |

FOREIGN PATENT DOCUMENTS

| | | |
|---|---|---|
| EP | 0089167 | 10/1986 |
| EP | 0290211 | 11/1988 |
| EP | 0244944 | 1/1990 |
| EP | 0459666 | 12/1991 |
| EP | 0795327 | 9/1997 |
| WO | 0220342 | 11/1992 |
| WO | 9310779 | 6/1993 |
| WO | 9628185 | 9/1996 |

OTHER PUBLICATIONS

Elliott, et al.; Feline chronic renal failure: clinical findings in 80 cases diagnosed between 1992 and 1995; Journal of Small Animal Practice (1998) 39, 78–85.
A.R. Michell; Progression of chronic renal failure: have we progressed?; The Veterinary Annual (1995) 35:159–176.
Finco, et al.; Progression of chronic renal disease in the dog; J. Vet. Intern Med. (1999) 13:516–528.
J.M. Bright; Feline Hypertension: Therapeutic Strategies; Proc. 17$^{th}$ACVIM, Chicago (1999), pp. 134–135.
Brown; Evaluation of chronic renal disease: A staged approach; Compendium on Cont. Ed. For the Practicing Vet, (1999) vol. 21: pp. 752–763 (1999).
Henik, et al.; Treatment of systemic hypertension in cats with amlodipine besylate; J. Am. Animal Hosp. Assoc., (1997), vol. 33 pp. 226–234.
Snyder; Amlodipine: A randomized, blinded clinical trial in 9 cats with systemic hypertension; J. Vet. Intern. Med. (1998) pp. 157–162.
Cooke, et al.; Calcium channel blockers in veterinary medicine; J. Vet. Intern. Med. (1998) 12: 123–131.
Reams, et al.; Amlodipine therapy corrects renal abnormalities encountered in the hypertensive state; Am. J. of Kidney Diseases; (1987) vol. X, No. 6 pp. 446–451.
Pearce, et al.; Calcium antagonists and the kidney; New Horizons (1996) vol. 4 No. 1 pp. 123–128.
Tobli, et al.; Effects of Amlodipine on Tubulointerstitial Lesions in Normotensive Hyperoxaluric Rats; Hypertension; vol. 34 Part II, p. 854–858 (1999) XP–001041746.
Raman, et al.; Renal effects of amlodipine in normotensive renal transplant receipients; Nephrol Dial Transplant; 14:384–388 (1999).
Raman, et al.; Modifying effects of amlodipine on cyclosporin A–induced changes in renal function in patients with psoriasis; Hypertension; Article S39–S41 (1999) XP–001041741.
Snyder, et al.; A Randomized, Blinded Clinical Trial in 9 Cats with Systemic Hypertension; J. Vet. Intern. Med.; 12:157–162 (1998) XP–001041936.
Amlodipine Besylate; Cardiovascular Drugs; p. 822–823 (1999) XP–002184526.
P.S. Synder; Evaluation of the Antihypentensive Agent Amlodipine Besylate in Mormotensive cats and cat with systemic hypetension; J. Vet. Intern. Med.; vol. 8, p. 147 (1994) XP–001042122.

* cited by examiner

Primary Examiner—Ray Henley
(74) Attorney, Agent, or Firm—Paul H. Ginsburg; Lorraine B. Ling; Kohn & Associates, PLLC

(57) ABSTRACT

The invention described herein relates to the use of calcium channel blockers such as amlodipine in the treatment of renal disease in normotensive animals. Also described are new unit doses of amlodipine suitable for the treatment of renal disease in normotensive cats.

5 Claims, No Drawings

TREATMENT OF RENAL DISORDERS

CROSS REFERENCE TO RELATED APPLICATIONS

This application claims the benefit of U.S. Provisional Application Ser. No. 60/198,415, filed Apr. 19, 2000. This application further claims benefit from United Kingdom Application no. GB 0008332.9, filed Apr. 4, 2000.

This invention relates to the treatment of renal disease in animals, especially chronic renal failure.

Renal disease, including renal failure (acute and chronic) is a common clinical problem which tends to increase with the age of animals (including humans). Conditions are described in "The Merck Manual", 16th edition, ch.149, pp.1661,1665 (Merck Research Laboratories (1992), and are commonly, but not always, associated with abnormally high blood pressure (hypertension). Renal disease often results in long suffering periods where the patient endures uncomfortable and painful symptoms, often involving injury to eyes, heart and brain. Dialysis and kidney transplantation can be used as treatments if circumstances allow, but these procedures can have serious complications, including, for transplantation, organ rejection.

In animals the underlying aetiology of the disease can be uncertain, even when histopathological examination has taken place (see e.g. J. Elliott and P J Barber, *J.Small Animal Practice* (February 1998) vol.39, 78; A R Michell, *Vet.Annual* (1995) 35:159).

There are many commonly used measurements of renal function such as those mentioned by D R Finco et al, in *J Vet Intern Med* (1999) 13:516–528—glomerular filtration rate (GFR), plasma creatinine concentration, morphologic examination of kidney tissue, blood urea nitrogen, incidental biological events such as hypertension and proteinurea. Michell (supra) defines chronic renal failure as a "failure of clearance". Finco (supra) suggests that declining GFR measurements are the most reliable indicator of the disease.

Treatment of renal disease associated with hypertension with antihypertensive agents has been propounded, for example with angiotensin converting enzyme (ACE) inhibitors, calcium channel blockers, etc. (see e.g. J M Bright, Proc.17th ACVIM, Chicago (1999), pp 134–135). Other treatments are mentioned by Brown, Scott A: Evaluation of chronic renal disease: A staged approach. Compendium on Continuing Education for the Practicing Veterinarian Vol 21: 752–763, 1999.

With regard to chronic renal failure associated with hypertension, treatment with amlodipine has been propounded, e.g. by:

Henik et al in *J.Am.Animal Hosp. Assoc.*, May/June 1997, vol.33);

P S Snyder, in *J. Vet.Intern. Med.*(1998): 12:157;

K L Cooke et al, in *J Vet. Intern. Med.* (1998); 12:123;

G P Reams et al, Am.J.Kidney Diseases (Dec 1987), vol X no.6, 446;

www.ccweb.net/marvistavet/html/body/chronic_renal_failure.html; and

C J Pearce et al, New Horizons (1996) vol.4 no. 1) 123.

Amlodipine, disclosed in EP 0 089 167, etc., is a dihydropyridine calcium channel blocker which is licensed for use as an antihypertensive and antianginal agent. It is sold as the besylate salt (disclosed in EP 0 244 944, etc.) in 2.5 mg, 5 mg and 10 mg dosages under the trade names Norvasc, Norvas, Istin, Amlor, etc. by Pfizer Inc. and related companies. Both of these publications are herein incorporated by reference.

We have now surprisingly found that calcium channel blockers such as amlodipine (e.g. as the besylate salt) can be used to treat renal disease in animals which are not hypertensive, i.e. animals which are "normotensive". "Normotensive" means having systemic arterial blood pressure values within normal or reference ranges established for the animal species of interest, using acceptable methods for measuring such blood pressure under appropriate circumstances, and below generally accepted "hypertensive" ranges for such animals. Within an animal species, reference range values may be established for representative subclasses, races, breeds, etc. (e.g. humans, lab. animals, specific subpopulations, etc.).

The prior art does not disclose or suggest that renal disease in normotensive patients, especially normotensive companion animals such as cats, can be treated with a calcium channel blocker such as amlodipine.

An aspect of the current invention is the treatment of renal disease in normotensive animals with a calcium channel blocker.

Preferably the animal is a mammal.

A preferred mammal is a human.

Another preferred group of mammals are companion animals such as horses, and domestic cats and dogs.

The most preferred companion animal is a domestic cat.

Preferably the renal disease is chronic renal failure.

Preferably the calcium channel blocker is a dihydropyridine calcium channel blocker such as amlodipine, nifedipine, nitrendipine, nimodipine, nicardipine, felodipine, etc.

The calcium channel blocker can be present as a pharmaceutically acceptable salt or solvate thereof. Pharmaceutically acceptable salts and solvates are non-toxic to the species being treated.

Suitable pharmaceutically acceptable salts for dihydropyridine calcium channel blockers include acid addition salts such as the hydrochloride, hydrobromide, hydroiodide, bisulphate, acid citrate, bitartrate, ethansulphonate, sulphate, phosphate or acid phosphate, acetate, maleate, fumarate, lactate, tartrate, citrate, gluconate, benzenesulphonate (besylate), p-toluenesulphonate (tosylate), methanesulphonate (mesylate), succinate, salicylate, nitrate, etc.

More preferably the calcium channel blocker is amlodipine and the pharmaceutically acceptable salts thereof, including acid addition salts such as the hydrochloride, hydrobromide, hydroiodide, bisulphate, acid citrate, bitartrate, ethansulphonate, sulphate, phosphate or acid phosphate, acetate, maleate, fumarate, lactate, tartrate, citrate, gluconate, benzenesulphonate (besylate), p-toluenesulphonate (tosylate), methanesulphonate (mesylate), succinate, salicylate, nitrate, etc.

Most preferred is the amlodipine besylate salt.

"Pharmaceutically acceptable" and related phrases mentioned herein include the corresponding veterinary equivalents.

"Treatment" refers to prevention, alleviation and/or cure of the condition.

Another aspect of the invention is the administration, to a normotensive animal, of an efficacious amount of a calcium channel blocker, such as between 0.01 to 3 mg/kg, preferably between 0.1 mg/kg and 0.3 mg/kg, more preferably between 0.12 and 0.25 mg/kg, amlodipine (preferably administered as the besylate salt) of the animal to treat renal disease such as chronic renal failure.

Another aspect of the invention is a unit dosage form of amlodipine which comprises about 0.1–1.5 mg, preferably about 0.2–0.6, or about 0.8 to 1.5 mg, most preferably about 0.1, 0.2, 0.4, 0.6, 0.8, 1.0, 1.2 or 1.5 mg amlodipine per unit, where amlodipine is preferably present as its besylate salt, suitable for, or adapted for, the treatment of normotensive cats with renal disease, such as chronic renal failure. Such unit doses can also be used to treat renal disease in animals with hypertension.

Optionally the calcium channel blocker can be administered/formulated with an antihypertensive agent of a different class (i.e. not another calcium channel blocker) such as an agent which reduces the effect of angiotensin and/or endothelin (defined herein as "other active agents").

Suitable agents include angiotensin converting enzyme (ACE) inhibitors such as those licensed for use in treating hypertension, such as benazepril, benazeprilat, captopril, enalapril, enalaprilat, fosinopril sodium, lisinopril, pentopril, perindopril, quinapril hydrochloride, quinaprilat, ramipril, ramiprilat, trandolapril, zofenopril calcium, and the like.

Certain combinations of calcium channel blockers and ACE inhibitors are disclosed in International Patent Application publication no. WO 96/28185, which is herein incorporated by reference.

For such combination therapies, co-administration may take place in a number of different ways, including:
 the active agents may be present in the same dosage form for single administration;
 the active agents may be administered in separate dosage forms, by the same or different administration routes, and at the same, substantially the same or at different times.

A suitable ACE inhibitor for co-administration in the treatment of renal disease is thought to be benazepril, currently marketed as Fortekor™, which for cats is administered at about 0.5 to about 1 mg/kg per day for cats as a 2.5 mg or 5 mg dose.

The calcium channel blockers (and/or other active agents) can be administered alone but will generally be administered in admixture with a suitable pharmaceutical excipient, diluent or carrier selected with regard to the intended route of administration and standard pharmaceutical or veterinary practice. Suitable pharmaceutical carriers, excipients, diluents, etc. can be found in Remington's Pharmaceutical Science, A. Osol, a standard reference text in the field.

For example, the calcium channel blocker (and/or other active agents) can be administered orally, buccally or sublingually in the form of tablets, capsules, ovules, elixirs, syrups, boluses, powders, pastes, drenches, medicated food or drinking water or other liquid, solutions or suspensions, which may contain flavouring or colouring agents, for immediate-, delayed-, modified-, sustained-, pulsed- or controlled-release applications.

Such tablets may contain excipients such as microcrystalline cellulose, silicified microcrystalline cellulose, lactose, sodium citrate, calcium carbonate, dibasic calcium phosphate and glycine, disintegrants such as starch (optionally pre-gelatinised, preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Additionally cyclodextrin solublity modifiers may be included. Additionally antioxidants may be included. Agents to improve palatability, such as flavouring agents (e.g. yeast, yeast extract, pork liver) may also be included. The agents apart from the calcium channel blocker may be present in intimate mixture with the calcium channel blocker, or they may be separated, e.g. in a bilayer, trilayer or other multlayer tablet or coated tablet, or a microparticulate capsule.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the calcium channel blockers (and/or other active agents) may be combined with various sweetening or flavouring agents, colouring matter or dyes, with emulsifying and/or suspending agents and with diluents such as water, ethanol, propylene glycol and glycerin, and combinations thereof.

The calcium channel blockers (and/or other active agents) can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution, or sterile aqueous or oil suspension, which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The calcium channel blockers (and/or other active agents) can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the calcium channel blocker (and/or other active agents) can be administered in the form of a suppository or pessary, or may be applied topically in the form of a gel, a pour-on, spot-on, dip, spray, mousse, shampoo, collar or powder formulation, ear tag, hydrogel, lotion, solution, cream, gel, paste, patch, ointment or dusting powder. The calcium channel blockers (and/or other active agents) may also be dermally or transdermally administered, for example, by the use of a skin patch. They may also be administered by the pulmonary or rectal routes.

For application topically to the skin, the calcium channel blocker (and/or other active agents) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

As an alternative for treating animals, the compounds may be administered with the animal feedstuff and for this purpose a concentrated feed additive or premix may be prepared for mixing with the normal animal feed.

For treatment of companion animals, further delivery devices are envisioned within the scope of this invention, such as the "chew" or masticable formulations mentioned in GB Patent application nos. 0007112.6 and 0010846.4, and the references therein. These formulations include:

an oral formulation for a medicament comprising:
a solid masticable portion and one or more reservoir portions encompassed by said solid masticable portion;
the solid masticable portion consisting of a fully edible material, having a Young's modulus of 0.01–5 MPa, and compressive strength in the range 10–10,000 mJ,
the reservoir portion or portions comprising a releasable dose of the medicament in a fluid (preferably a liquid) form, with a viscosity below 800 mPa.s at body temperature (ca. 36–ca.40° C.),
such that on mastication, the masticable portion is ruptured and the unit dose of the medicament is released in a short space of time from the reservoir portion into the oral cavity.

The calcium channel blockers (and/or other active agents mentioned above) can also be administered together with yet further active agents should the medical need arise.

The physician or veterinarian in any event will determine the actual dosage which will be most suitable for any individual patient and it will vary with the age, weight and response of the particular patient. The dosages mentioned herein are exemplary of the average case. There can, of course, be individual instances where higher or lower dosage ranges are merited and such are within the scope of this invention. The skilled person will appreciate that, in the treatment of certain conditions the compounds may be taken as a single or multiple dose as needed or desired.

The route of administration will depend on a number of factors, and in accordance with standard medical and veterinary practice, including the species of animal to be treated, size of the animal, ease of administration, etc.

Based on the results disclosed herein, the envisioned dosage regime for amlodipine in the treatment of renal disease, such as chronic renal failure, in normotensive animals, is 0.125–0.25 mg/kg/day.

For the treatment of renal disease in normotensive (and hypertensive) domestic cats the envisioned amlodipine dosage regime is 0.125–0.25 mg/kg/day, which translates to 0.4 mg/cat/day for cats weighing from 1.6 kg up to about 3 kg, 0.8 mg/cat/day for cats weighing between 3–6.5 kg, and 1.2 mg/cat/day for cats weighing about 6.5–9.5 kg. Cats falling outside these weight ranges will of course be treatable in proportion to their weight. Oral administration is preferred, preferably of a tablet.

Benazepril may be co-administered at 0.5 to 1 mg/kg per day, e.g. as a 2.5 mg or 5 mg dose for domestic cats (as in Fortekor™ mentioned above). Other ACE inhibitors and/or endothelin-reducing agents may be co-administered with the calcium channel blocker such as amlodipine according to the medical need, efficacy, etc.

The efficacy of calcium channel blockers such as amlodipine in the treatment of chronic renal failure, in the dosages mentioned and with the populations mentioned can be demonstrated by measurement of renal function (e.g. by GFR measurements or any other measurements known in the art such as renal plasma flow using appropriate markers such as creatinine, inulin, iohexol, radioisotopes and other validated markers of dynamic renal function, urine concentrations of analytes such as protein and/or protein indexed to urine creatinine concentration, etc.). Measurements can be made before treatment, during treatment and after treatment by methods well-known in the art. For control purposes, a similar population can be treated with a placebo instead of a calcium channel blocker. Efficacy studies should be appropriately controlled for concurrent disease conditions, drug treatments, diet etc. that may confound the interpretation of data used to assess treatment of renal failure, and appropriate statistical analyses applied to variables.

For measurement of blood pressure, e.g. to define the normotensive subpopulation, there are numerous methods mentioned in the art, such as that disclosed by P S Snyder, in *J. Vet.Intern. Med.*(1998): 12:157. Henik (supra) defines hypertension in cats as a blood pressure of 170 mm Hg or more. Some other workers in the field define the level at 175 mm Hg or more.

Biological Data

EXAMPLE 1

In this experiment, comparative groups of normotensive nephrectomised cats with chronic renal failure had their GFR measured. One group received placebo and the other received amlodipine besylate once daily at 0.125 mg/kg. After 35 days the GFR was measured again. There was no change in the placebo group, but the GFR had increased by an average of ca. 28% for the amlodipine-treated group.

Amlodipine besylate at ca. 0.125 mg/kg to ca. 0.25 mg/kg was administered orally by tablet (0.2 mg, 0.4 mg, 0.8 mg and 1.2 mg) to normotensive cats (systolic blood pressure of 160 mm Hg or less as measured under standard conditions) once daily for a number of weeks, and measurements made at intervals to measure the effect on kidney function in cats presented as veterinary patients with renal problems. In parallel, a number of cats were treated with an oral placebo tablet. Various breeds and crossbreeds of cats of approximately 6 months of age or older were used in the trial. Initial weights of 0.8 kg to 9.6 kg were chosen, and the cats were either males or non-pregnant females (entire or neutered). For each animal, the body weight was used to select the appropriate tablet potency of amlodipine (0.125 to 0.25 mg/kg/day) according to the following table:

| Body Weight | | Tablet Potency (mg) |
|---|---|---|
| Kilograms (kg) | Pounds (lb) | |
| 0.8 to 1.5 | 1.8 to 3.5 | 0.2 |
| 1.6 to 3.0 | 3.6 to 7.0 | 0.4 |
| 3.1 to 6.5 | 7.1 to 14.0 | 0.8 |
| 6.6 to 9.5 | 14.1 to 21.0 | 0.8 + 0.4 |

Each of the amlodipine tablets used in the study were complemented by placebo tablets with the same excipients and which had the same dimensions and appearance.

Particular amlodipine besylate tablets used had the following compositions:

| Names of Ingredients | Composition (mg/unit) |
|---|---|
| Amlodipine Besylate[1] | 0.278 |
| Microcrystalline Cellulose | 64.481 |
| Calcium Hydrogen Phosphate, Anhydrous | 32.241 |
| Sodium Starch Glycollate | 2.000 |
| Magnesium Stearate | 1.000 |
| Total | 100.000 mg |

Presentation: 6.0 mm standard round convex white tablet with no engraving

[1]Equivalent to 0.2 mg of amlodipine calculated on a theoretical activity of 72%.

| Names of Ingredients | Composition (mg/unit) |
|---|---|
| Amlodipine Besylate[2] | 0.556 |
| Microcrystalline Cellulose | 64.296 |
| Calcium Hydrogen Phosphate, Anhydrous | 32.148 |
| Sodium Starch Glycollate | 2.000 |
| Magnesium Stearate | 1.000 |
| Total | 100.000 mg |

Presentation: 6.0 mm standard round convex white tablet with no engraving

[2]Equivalent to 0.4 mg of amlodipine calculated on a theoretical activity of 72%.

| Names of Ingredients | Composition (mg/unit) |
|---|---|
| Amlodipine Besylate[3] | 1.111 |
| Microcrystalline Cellulose | 63.926 |
| Calcium Hydrogen Phosphate, Anhydrous | 31.963 |
| Sodium Starch Glycollate | 2.000 |
| Magnesium Stearate | 1.000 |
| Total | 100.000 mg |

Presentation: 6.0 mm standard round convex white tablet with no engraving

[3]Equivalent to 0.8 mg of amlodipine calculated on a theoretical activity of 72%.

The tablets were prepared using standard blending and direct compression techniques. The tablets described herein used the same excipients and manufacturing processes as the commercially available tablets.

Biological Data—Experiment 2

The data in the Table below were collected from client-owned, pet cats that had been diagnosed with spontaneous chronic renal failure (chronic renal insufficiency). These cats were presented by owners/clients to veterinary practices for evaluation of general health, kidney function, and systolic blood pressure.

Chronic renal failure is generally considered an irreversible and progressive disease in cats. Chronic renal failure was diagnosed in each cat in this study. Cats were considered normotensive as defined by systolic arterial blood pressure less than 160 mm Hg prior to the onset of treatment. Cats were randomly assigned to treatment with either amlodipine besylate tablets at 0.125 to 0.25 mg/kg (as described above) or placebo tablets administered once daily by the oral route.

Renal function was assessed by determining glomerular filtration rate (GFR). GFR was estimated from plasma clearance of the exogenous marker, iohexol, approximately 7 days prior to the onset of treatment (day—7) and on approximately days 28, 56, 112, and 224 following onset of treatment.

Table—Glomerular filtration rate (mL/min/kg) in cats with chronic renal failure treated once daily by the oral route with either amlodipine besylate at 0.125 to 0.25 mg/kg or placebo

| Day of Study | −7 | 28 | 56 | 112 | 224 |
|---|---|---|---|---|---|
| Treatment Amlodipine | | | | | |
| Mean GFR | 0.76 | 0.80 | 0.78 | 0.85 | 0.83 |
| Std Deviation | 0.29 | 0.36 | 0.26 | 0.31 | 0.26 |
| Number of Cats | 10 | 9 | 10 | 9 | 10 |
| Placebo | | | | | |
| Mean GFR | 0.90 | 0.89 | 0.92 | 0.85 | 0.75 |
| Std Deviation | 0.23 | 0.22 | 0.22 | 0.23 | 0.30 |
| Number of Cats | 13 | 12 | 12 | 13 | 13 |

In cats receiving amlodipine, GFR increased on average 9% between day −7 and day 224. In contrast, placebo-treated animals experienced a decline in GFR of 17% between day −7 and day 224. These data demonstrate that amlodipine besylate at 0.125 to 0.25 mg/kg/day orally prevents the decline in function associated with the progression of chronic renal failure in cats.

Examples of formulations offering 0.4 mg and 0.8 mg amlodipine respectively, based on a potency of 72.1%, which demonstrated robustness and good stability are described below. These were made by standard direct compression techniques well known in the art.

| | Components | Quantity/Unit mg/tablet | |
|---|---|---|---|
| 1 | Amlodipine besylate | 0.555 | (a) |
| 2 | Microcrystalline cellulose | 42.963 | (b) |
| 3 | Calcium hydrogen phosphate, anhydrous | 21.482 | |
| 4 | Sodium starch glycollate (type A) | 4.000 | (c) |
| 5 | Dried yeast | 30.000 | (d)(d) |
| 6 | Magnesium stearate | 1.000 | |
| | | 100.000 | |
| 1 | Amlodipine besylate | 1.110 | (e) |
| 2 | Microcrystalline cellulose | 42.593 | (b) |
| 3 | Calcium hydrogen phosphate, anhydrous | 21.297 | |
| 4 | Sodium starch glycollate (type A) | 4.000 | (c) |
| 5 | Dried yeast | 30.000 | (d)(d) |
| 6 | Magnesium stearate | 1.000 | |
| | | 100.000 | |

Footnotes:
(a) Equivalent to 0.4 mg/tablet of based on a potency of 72.1%
(b) As Avicel PH102 ™
(c) As Explotab CLV ™
(d) As Debittered brewers yeast 1330
(e) Equivalent to 0.8 mg/tablet of based on a potency of 72.1%

What is claimed is:

1. A method of treating renal disease in normotensive animals comprising administration of an effective amount of a calcium channel blocker, optionally in the presence of an antihypertensive agent that reduces the effect of endothelin and/or angiotensin.

2. The method according to claim 1 wherein the calcium channel blocker is a dihydropyridine.

3. The method according to any of claims 1 or 2 wherein the calcium channel blocker is amlodipine.

4. A method of treating renal disease in normotensive animals comprising administration of an effective amount of a calcium channel blocker, wherein the calcium channel blocker is amlodipine besyate, optionally in the presence of an antihypertensive agent of a different class.

5. The method according to claim 4 wherein said antihypertensive agent of a different class in an agent that reduces the effect of endothelin and/or angiotensin.

* * * * *